United States Patent [19]
Letchworth

[11] Patent Number: 5,437,649
[45] Date of Patent: Aug. 1, 1995

[54] ADJUSTABLE BODY OPENING DILATOR

[76] Inventor: William A. Letchworth, 1101 Peachtree Rd., Wilson, N.C. 27894

[21] Appl. No.: 323,798

[22] Filed: Oct. 17, 1994

[51] Int. Cl.$^6$ .............................................. A61M 31/00
[52] U.S. Cl. ........................................ 604/278; 600/32
[58] Field of Search ................ 604/277, 278, 327–332; 600/29–32

[56] References Cited

U.S. PATENT DOCUMENTS

| | | | |
|---|---|---|---|
| 1,616,389 | 2/1927 | Piercy | 604/278 |
| 1,969,831 | 8/1934 | Williams | 604/278 |
| 2,649,854 | 8/1953 | Salm | 600/29 |
| 5,336,203 | 8/1994 | Goldhardt et al. | 604/332 |

FOREIGN PATENT DOCUMENTS 3613696  10/1987  Germany .............................. 600/29

*Primary Examiner*—Jerome L. Kruter
*Attorney, Agent, or Firm*—Rhodes, Coats & Bennett

[57] ABSTRACT

The present invention entails a body opening dilator for dilating opening of the body such a stoma or a rectal opening. The dilator includes an expandable screw actuated insert that is adapted to be inserted into the body opening. Disposed within the expandable insert is a flexible expander that is engaged by the screw. By turning the screw, the expander is moved outwardly against the surrounding wall of the expandable insert causing the same to expand. A fluid channel is provided within the screw for pertaining fluid to be directed into and through the expandable insert. Formed about the inner end of the expandable insert is a dispersing opening that directs the fluid from the expandable insert into the patient.

4 Claims, 2 Drawing Sheets

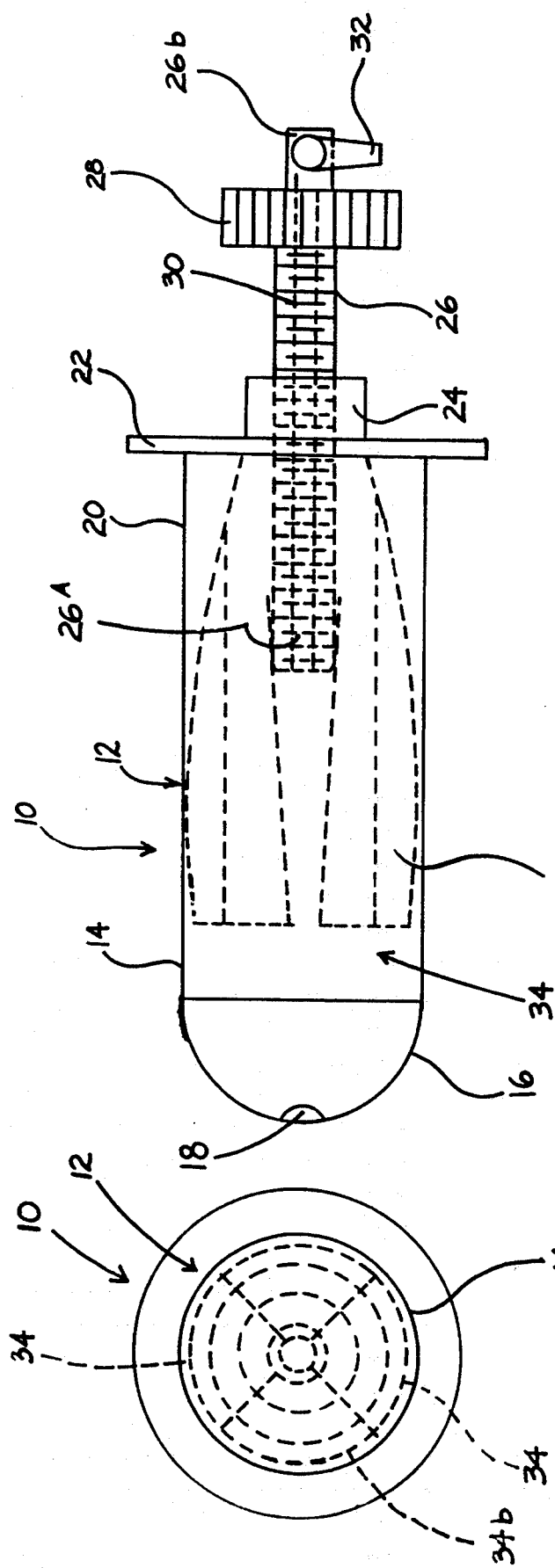

ADJUSTABLE BODY OPENING DILATOR

FIELD OF THE INVENTION

The present invention relates to surgery and more particularly to a dilator for dilating body openings such as stoma and rectal openings.

BACKGROUND OF THE INVENTION

There are many individuals that have to deal with the problems and inconveniences of a colostomy. One such problem is that of maintaining a well-healed and fully open colostomy opening. The problem is that over time the colostomy opening has a natural tendency to heal and become closed. This presents problems to the patient that is attempting to insert the appropriate apparatus into the colostomy opening in order to effectuate a bowel movement. Again, the problem centers around the colostomy opening tending to heal and close. Because of this, the patient continues to experience pain and discomfort often as he or she attempts to insert the appropriate structure or apparatus to effectuate bowel movements into the colostomy opening.

Therefore, there is a need for a device that can be worn by the patient that will maintain the colostomy opening fully opened such that the appropriate apparatus used to instigate bowel movements can be easily and without pain inserted into the patient.

SUMMARY AND OBJECTS OF THE INVENTION

The present invention entails a dilator that is designed to be worn by a patient having a colostomy opening or used to dilate a body opening. The dilator functions to maintain the colostomy opening fully opened, and worn periodically for selected periods of time the dilator serves to prevent the colostomy opening from closing and healing over as is the natural tendency of such a body wound. The dilator or stoma dilator of the present invention entails an expandable insert that is inserted directly into the colostomy or body opening. A flexible expander disposed internally within the expandable insert is engaged with a screw actuator which when turned is operative to engage the flexible expander causing the same to move outwardly and engage the moveable wall of the expandable insert causing the expandable insert to expand, thereby increasing the effective diameter or opening size of the patient's colostomy opening.

It is therefore an object of the present invention to provide a stoma dilator for a colostomy opening that can be worn by the patient periodically for the purpose of maintaining the colostomy opening fully opened.

Another object of the present invention resides in the provision of a body opening dilator that is suitable for use in dilating and maintaining a wide variety of body openings including a rectal opening.

Still a further object of the present invention resides in the provision of a dilator of the character referred to above that is relatively simple in design and which can in fact be inserted, operated and manipulated by the patient.

Still a further object of the present invention resides in the provision of a stoma dilator of a character referred to above that itself is capable of transmitting fluids to and from the patient.

Other objects and advantages of the present invention will become apparent and obvious from a study of the following descriptions and the accompanying drawings which are merely illustrative of such invention.

BRIEF DESCRIPTION OF THE DRAWINGS

FIG. 1 is a side elevational view of the dilator of the present invention

FIG. 2 is an end view of a dilator of the present invention.

DETAILED DESCRIPTION OF THE INVENTION

Figure 3:
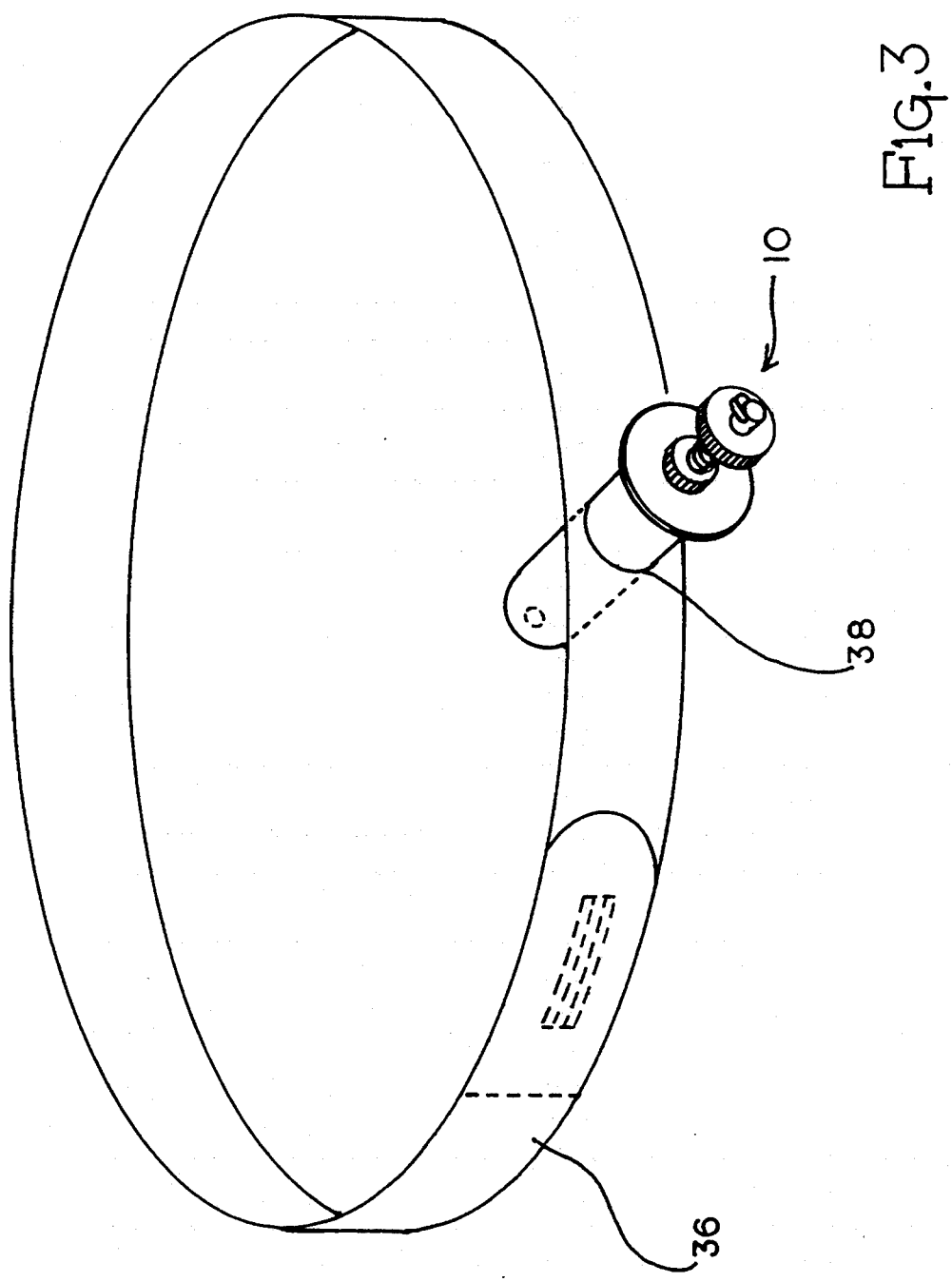
FIG. 3 is a view illustrating a belt provided with the dilator for supporting the same within the patient.

With further reference to the drawings, the body opening dilator of the present invention is shown therein and indicated generally by the numeral 10.

Dilator 10 comprises an expandable insert indicated generally by the numeral 12. Expandable insert 12 includes a moveable (expandable) wall 14 that is made from a pliable or flexible material such as rubber. The expandable insert 12 further includes an entry end portion 16 that includes a spherical shaped end and includes a fluid outlet 18. Opposite the entry end portion 16 is an outside or exterior end portion indicated by the numeral 20. The exterior end portion 20 includes a flange 22 that includes an opening formed therein. Co-axial with the opening formed in the flange 22 is a threaded sleeve 24 that receives a threaded screw 26 that extends into the interior hollow portion of the expandable insert 12. Screw 26 includes an inner end portion 26a and an outer end portion 26b. Secured about the outer end portion 26b of the screw 26 is a thumb wheel 28.

In addition, screw 26 includes an axial fluid inlet channel 30 that extends completely through the screw and enables fluid or water to be directed into the interior hollow portion of the expandable insert 12. Note, there is formed a control valve 32 about the outer end portion 26b of the screw 26 that enables the fluid inlet channel 30 to be opened or closed.

Disposed within the interior of the expandable insert 12 is a flexible expander 34 that works in conjunction with the interior end 26a of the screw to expand the outer wall 14 of the expandable insert 12. The flexible expander 34 is made of a flexible resilient material such as rubber and includes a series of expandable elements or segments 34a, 34b, 34c, and 34d. The flexible expander 34 is anchored to the outside end portion 20 of the expandable insert 12. A central opening exist within the flexible expander 34 that receives the inner end portion 26a of the screw 26. It is seen in the drawings that the inner end 26a extends into the central opening formed within the various expander segments 34a, 34b, 34c, and 34d. As the screw 26 is moved axially back and forth, the inner end portion 26a engages the various expander segments of the flexible expander 34, and this results in the flexible expander moving outwardly and inwardly. Because of the flexible resilient nature of the flexible expander 34, the same will move back to its inner position due to the resilient nature of the rubber material that comprises the expandable segments 34a, 34b, 34c, and 34d.

Also shown in the drawings is a belt 36 that is designed to receive and support the dilator 10 of the present invention. Belt 36 includes an opening 38 that can be appropriately aligned with the body opening or colostomy opening such that the dilator 10 can be inserted through the belt opening 38 and on through the body opening. Note that the flange 22 formed about the exterior end portion 20 will engage and butt against a portion of the belt 36 surrounding the belt opening 38.

In operation, the expandable insert 12 may be inserted into a body opening formed within a patient. This could be a colostomy opening or a rectal opening or other type of body opening. If used in conjunction with the belt 36, the flange 22 is positioned adjacent the belt with the inner end portion 16 extending into the patient's body. To discourage the closing or healing of the body opening, the dilator 10 can be expanded so as to expand and hold open the particular body opening. In the present case, the dilator 10 is expanded by screwing screw 26 such that its inner end 26a moves towards the entry end portion 16 of the expandable insert 12. As the screw so moves, the inner end portion 26 engages the flexible expander and causes the flexible expander to move outwardly. As the respective expandable segments engage the outer wall 14 of the expandable insert 12, the outer wall 14 tends to bulge and expand causing the body opening through which the dilator extends to also expand. Once a selected expansion is achieved, the patient can simply maintain the dilator in the body opening for a selected period of time. It is contemplated that the dilator 10 would be maintained within the body opening for selective periods of time and would be periodically worn by the patient so as to discourage the closing of healing of the body opening.

In order to remove the dilator 10, the screw 26 is turned such that the inner end 26a moves towards the outside or the exterior end portion 20 of the expandable insert 12. Because the flexible expander 34 is biased to move inwardly, the respective expander segments 34a, 34b, 34c and 34d move inwardly as the screw 26 is turned and the inner end 26a moves towards the flange 22. Thus, the flexible expander moves inwardly away from the outer movable resilient wall 14 of the expandable insert 12. This results in the moveable wall 14 decreasing in effective diameter. Once pressure has been released from the moveable wall 14 the dilator 10 can be removed from the patient's opening.

It should also be appreciated that water can be directed into and out of the patient, via the dilator 10. In particular, the patient's intestines can be flushed by directing fluid by gravity into the inlet end of the fluid inlet 30 formed in screw 26. The fluid or water will enter the inner chamber of the expandable insert 12 and will be dispersed into the patient, via the fluid outlet 18.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended Claims are intended to be embraced therein.

What is claimed is:

1. A stoma dilator adapted to be inserted within an opening formed in the human body such as a colostomy opening, comprising:
   (a) an insert having a continuous and closed resilient outer expandable wall, an entry end portion, and an exterior end portion;
   (b) the continuous and closed outer expandable wall of the insert being movable between an expanded state and a relaxed state;
   (c) a tapered flexible expander disposed interiorly within the insert and lying adjacent the expandable wall, the flexible expander being laterally moveable independently of the expandable wall;
   (d) a screw cavity formed interiorly of the flexible expander and extending between the entry end portion and the exterior end portion of the insert;
   (e) an actuating screw extending into and through at least a portion of the screw cavity for directly engaging the surface of the flexible expander and for moving the flexible expander outwardly for engagement with the expandable wall of the insert such that as the actuator screw is turned and the flexible expander moves outwardly, the engagement of the flexible expander with the expandable wall of the insert causes the expandable wall of the insert to expand; and
   (f) an elongated fluid transfer channel formed in the actuator screw and having an inlet and an outlet end, the fluid transfer channel formed in the actuator screw functioning to direct fluid into the inlet end, through the fluid transfer channel, into the insert and into the human body, and to also channel fluid from the human body through the insert, into the fluid transfer channel and out the inlet end.

2. The stoma dilator of claim 1 wherein the flexible expander includes a series of expander elements that extend around the inner end portion of the screw.

3. The stoma dilator of claim 1 wherein the exterior end portion of the expandable insert includes a flange.

4. The stoma dilator of claim 3 including a belt adapted to be secured to a patient adjacent a body opening formed within the patient, and wherein the belt includes an opening formed therein through which the expandable insert may pass.

* * * * *